United States Patent
Nagatomi et al.

(10) Patent No.: US 8,329,624 B2
(45) Date of Patent: Dec. 11, 2012

(54) ORGANIC MOLYBDENUM COMPOUNDS AND LUBRICATING COMPOSITIONS WHICH CONTAIN SAID COMPOUNDS

(75) Inventors: Eiji Nagatomi, Tokyo (JP); Noriaki Shinoda, Tokyo (JP); Yoshihiko Aihara, Tokyo (JP)

(73) Assignee: Shell Oil Company, Houston, TX (US)

( * ) Notice: Subject to any disclaimer, the term of this patent is extended or adjusted under 35 U.S.C. 154(b) by 683 days.

(21) Appl. No.: 12/525,359

(22) PCT Filed: Feb. 1, 2008

(86) PCT No.: PCT/EP2008/051258
§ 371 (c)(1),
(2), (4) Date: Nov. 25, 2009

(87) PCT Pub. No.: WO2008/092946
PCT Pub. Date: Aug. 7, 2008

(65) Prior Publication Data
US 2011/0312863 A1    Dec. 22, 2011

(30) Foreign Application Priority Data
Feb. 1, 2007    (JP) .................. 2007-023479

(51) Int. Cl.
C08K 5/56 (2006.01)
C10M 135/18 (2006.01)
C07F 11/00 (2006.01)

(52) U.S. Cl. ............. 508/382; 508/383; 556/57; 556/58

(58) Field of Classification Search .................. 508/382, 508/383; 556/57, 58
See application file for complete search history.

(56) References Cited

U.S. PATENT DOCUMENTS 5,126,465 A    6/1992    Greaney et al. ............. 556/61

FOREIGN PATENT DOCUMENTS

| | | |
|---|---|---|
| DE | 3717143 | 12/1988 |
| EP | 0668342 | 8/1995 |
| EP | 0776959 | 6/1997 |
| EP | 1029029 | 4/1999 |
| EP | 1741772 | 10/2007 |
| GB | 789383 | 1/1958 |
| JP | 48056202 | 8/1973 |
| JP | 52019629 | 2/1977 |
| JP | 52106824 | 9/1977 |
| JP | 62161992 | 7/1987 |
| JP | 3495764 | 2/2004 |
| WO | WO9721788 | 6/1997 |
| WO | WO9941332 | 8/1999 |
| WO | WO0008115 | 2/2000 |
| WO | WO0014179 | 3/2000 |
| WO | WO0014183 | 3/2000 |
| WO | WO0014187 | 3/2000 |
| WO | WO0014188 | 3/2000 |
| WO | WO0015736 | 3/2000 |
| WO | WO0118156 | 3/2001 |
| WO | WO0157166 | 8/2001 |

OTHER PUBLICATIONS

Domrachev, G.A., et al: "Molybdenum disulfide formation during decomposition of organic compounds containing a molybdenum-sulfur bond", XP002475834.

Cousins, M., et al: "Some oxo- and oxochlorocyclopentadienylmolybdenum complexes", XP002475835.

Green, Malcolm L.H., et al: Interconversion of oxo and imido ligands at a dimolybdenum center: molecular and electronic structure of [{Mo(.eta.—C5H4Me) (NPh) (.mu.—NPh)}], XP002475836.

Saurenz, Dirk, et al: "Cyclopentadienylmolybdenum(VI) and molybdenum(V) oxo chemistry: new synthetic and structural features", XP002475837.

Hogarth, Graeme, et al: "Electrochemistry of dimolybdenum complexes containing oxo, imido, and sulfide moieties. A measure of their relative .pi.—donor abilities?", XP002475838.

Bursten, Bruce E., et al: "Electronic structure of piano-stool dimers. 8. Electronically induced conformational changes in high-valent bimetallic chalcogen complexes of the type [CpML]2(.mu.—L)2 (M=molybdenum rhenium; L=S, O)", XP002475839.

Gun, Jenny, et al: "Reduction of [ (C5Me5)2Mo2O5] and [ (C5Me5)2Mo2O4] in methanol/water/trifluoroacetate solutions investigated by combined on-line electrochemistry/electrospray-ionization mass spectrometry", XP002475840.
Brunner, Henri, et al: "Preparation and reactivity of binuclear oxo(pentamethylcyclopentadienyl)molybdenum sulfides", Journal of Organometallic Chemistry, 331(1), pp. 45-52, 1987, XP002475832.
Journal of Organometallic Chemistry 331(1), pp. 45-52, XP002475833.
Tanner, L.D., et al: "Structures and reactivities of cyclopentadienylmolybdenum complexes with oxo and sulfide ligands", XP002475841.
Reuter, U. et al: "On chalcogenolates. LXX. Experiments to prepare tetrathiooxalates. About alkylthio-1, 3-dithiole-2-thiones" XP002476509.
Maejima, Seiju et al: "Surface reinforcement of an inorganic porous material" XP002473509.
Unoura, Kei et al: "Substituent effects of cis-dioxobis(dithiocarbamato)molybdenum(VI) on redox properties: redox potentials for one-electron reduction and second=order rate constants for oxygen atom transfer" XP002476206.
Sovilj, S. P. et al; "Molecular modelling of new dioxomolybdenum (VI) complexes with heteroalicyclic dithiocarbamates. In Silico models for metal-implant coating within living systems" XP002476207.
Gnecco, J. A. et al: "Catalytic epoxidation of cyclohexene using molybdenum complexes" XP002476208.
Sovilj, S. P. et al: "Dioxomolybdenum (VI) complexes of methylpiperidinodithiocarboxylates" XP002476209.
Macial, Benigno et al: "An EXAFS study of Mo(VI) and Mo (V) complexes with proline dithiocarbamate" XP002476210.
Stergiou, Anagnostis C. et al: "Spectroscopic investigation of dichloro and hydrazido(2-) derivatives of bis9dithiocarbamato)dioxomolybdenum(VI) compounds. Crystal and molecular structure of bis(diisobutyldithiocarbanato) (N,N-dimethylhydrazido(2-)-N')oxomolybdenum(VI)" XP002476211.
Bhat, G. S. et al: "Synthesis and characterization of lead(II), bismuth (III), titanium(IV), selenium(IV), thorium(IV), dioxomolybdenum(VI) and dioxouranium(VI), hexamithyleniminecarbodithioate and their biological activities" XP002476212.
Nair, B. Gopalakrishnan et al: "A novel series of cis-dioxomolybdenum(VI) carbodithioate complexes" XP002476213.
Moloy, Kenneth G.: "Oxygen atom transfer reactions, Epoxide deoxygenation by bis(diethyldithiocarbamato)oxomolybdenum" XP002476214.
Berzina, S. et al: "Two-phase stability constants of some 3-pyrorolecarbodithioates and 3-indoleacrbodithioates" XP002476215.
Byr'Ko, V. M. et al: "Composition and structure of mlybdenum (V, VI)5-phenyl-1-pyrazolinedithiocarbamates" XP002476216.

*Primary Examiner* — James Goloboy
*Assistant Examiner* — Vishal Vasisth (57) ABSTRACT

The present invention provides dicyclopentadienyl molybdenum crosslinked complexes which can be represented by general formula (1) below, the use thereof as friction-modifiers and lubricating compositions which contain these compounds.

General Formula (1)

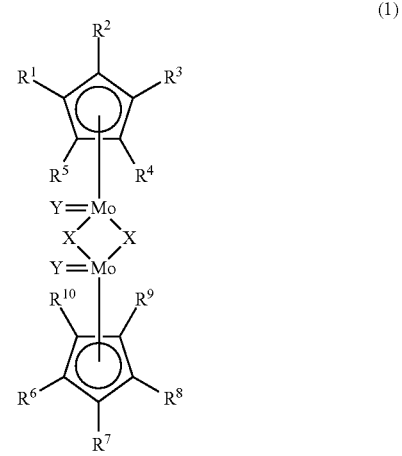

In this formula X is the element oxygen or the element sulphur, Y is the element oxygen or Y is absent, and $R^1$ to $R^{10}$ are groups selected individually from the group comprising hydrogen, the methyl group and the ethyl group.

7 Claims, 1 Drawing Sheet

ORGANIC MOLYBDENUM COMPOUNDS AND LUBRICATING COMPOSITIONS WHICH CONTAIN SAID COMPOUNDS

This application is a 371 of PCT/EP2008/051258, filed Feb. 1, 2008, which is incorporated by reference and which claims priority from JP 2007-023479, filed 1 Feb. 2007.

TECHNICAL FIELD OF THE INVENTION

The invention relates to novel organic molybdenum compounds, the use thereof as friction-modifiers and lubricating compositions which contain said compounds.

BACKGROUND OF THE INVENTION

Friction-modifiers (friction-adjusting agents) are used for adjusting the friction characteristics of a lubricant to an appropriate level. Friction-modifiers which reduce friction are used in lubricating compositions such as gear oils and engine oils with a view to reducing fuel costs. Friction-modifiers which raise friction are used for maintaining a certain high friction level in the lubricating compositions which are used in the wet-type clutch part of an automatic gear box. Many types of such friction-modifiers have been proposed.

The organic molybdenum compounds are the most typical of these friction-modifiers and, as shown in "Shinban Sekiyu Seihin Tenkasai" (New Edition, Additives for Petroleum Products), by Toshio SAKURAI, Saiwai Shobo Co., published 25 Jul., 1986, these organic molybdenum compounds are compounds which have two molybdenum atoms in one molecule as shown in formulae (2) and (3) below.

Formula (2)

(Dithiophospat Type)

Formula (3)

(Dithiocarbamate Type)

(Those compounds for which in this formulae x=0 and y=4, and for which x+y=4, and for which x≧2 are insoluble in oil and the others are oil-soluble.)

Furthermore, compounds in which the element molybdenum is included twice in one molecule have been disclosed in Japanese Patent No. 3495764, Japanese Examined Patent Publication 45-24562, Japanese Unexamined Patent Application Laid Open 52-19629, Japanese Unexamined Patent Application Laid Open 52-106824, and Japanese Unexamined Patent Application Laid Open 48-56202.

A problem with catalyst poisoning in the apparatus which is used for cleaning-up the exhaust gas arises when compounds which contain phosphorus in the molecule as shown in the aforementioned general formula (2) are added to engine oils and there is a demand for compounds which are phosphorus-free.

SUMMARY OF THE INVENTION

An object of the present invention is to provide novel compounds which are useful as lubricating additives and the like which do not contain phosphorus, which reduce the friction coefficient and control the friction of a wet-type clutch, for example, optimally, and friction modifiers comprising said compounds.

A further object of the invention is to provide lubricating compositions which contain these compounds.

DETAILED DESCRIPTION OF THE PREFERRED EMBODIMENTS

To achieve these objects, the present invention provides dicyclopentadienyl molybdenum crosslinked complexes having general formula (1) below.

General Formula (1)

In this formula X is the element oxygen or the element sulphur, Y is the element oxygen or Y is absent, and $R^1$ to $R^{10}$ are groups selected individually from the group comprising hydrogen, a methyl group and an ethyl group.

According to a preferred embodiment the dicyclopentadienyl molybdenum crosslinked complexes of general formula (1) can be represented by general formula (2) which is indicated below.

General Formula (2)

(2)

In this formula $R^1$ to $R^{10}$ are groups selected individually from the group comprising hydrogen, a methyl group and an ethyl group.

According to a preferred embodiment the dicyclopentadienyl molybdenum crosslinked complexes of general formula (1) can be represented by general formula (3) which is indicated below.

General Formula (3)

(3)

In this formula $R^1$ to $R^{10}$ are groups selected individually from the group comprising hydrogen, a methyl group and an ethyl group.

According to a preferred embodiment the dicyclopentadienyl molybdenum crosslinked complexes of general formula (1) can be represented by general formula (4) which is indicated below.

General Formula (4)

(4)

In this formula $R^1$ to $R^{10}$ are groups selected individually from the group comprising hydrogen, a methyl group and an ethyl group.

According to a preferred embodiment the dicyclopentadienyl molybdenum crosslinked complexes of general formula (1) can be represented by general formula (5) which is indicated below.

General Formula (5)

(5)

In this formula $R^1$ to $R^{10}$ are groups selected individually from the group comprising hydrogen, a methyl group and an ethyl group.

Further the present invention provides the use of the dicyclopentadienyl molybdenum crosslinked complexes as friction-modifiers.

Also the present invention provides lubricating compositions which contain the compounds.

The compounds of this invention can be produced, for example, using the method indicated below.

First Process

Synthesis of the Synthesis Intermediate Raw Material Dicyclopentadienyl Molybdenum Hexa-Carbonyl Complex

In these formulae $R^1$ to $R^{10}$ have the same significance as before.

Second Process

Synthesis of the Dicyclopentadienyl Molybdenum Crosslinked Complex

The di(cyclopentadienyl) μ-thioxomolybdenum complex of general formula (2), the di(cyclopentadienyl) μ-thioxodioxomolybdenum complex of general formula (3), the di(cyclopentadienyl) μ-oxomolybdenum complex of general formula (4) and the di(cyclopentadienyl) μ-oxodioxomolybdenum complex of general formula (5) are produced simultaneously in accordance with the reaction equation indicated below.

(5)

Hydrogen, the methyl group and the ethyl group can be cited for the aforementioned $R^1$ to $R^{10}$, and the compounds with combinations such as those shown in Tables 1 to 18 below can be cited.

TABLE 1

| Compound | 1 | 2 | 3 | 4 | 5 | 6 | 7 | 8 |
|---|---|---|---|---|---|---|---|---|
| X | S | S | O | O | S | S | O | O |
| Y | O | — | O | — | O | — | O | — |
| $R^1$ | H | H | H | H | $CH_3$ | $CH_3$ | $CH_3$ | $CH_3$ |
| $R^2$ | H | H | H | H | $CH_3$ | $CH_3$ | $CH_3$ | $CH_3$ |
| $R^3$ | H | H | H | H | $CH_3$ | $CH_3$ | $CH_3$ | $CH_3$ |
| $R^4$ | H | H | H | H | $CH_3$ | $CH_3$ | $CH_3$ | $CH_3$ |
| $R^5$ | H | H | H | H | $CH_3$ | $CH_3$ | $CH_3$ | $CH_3$ |
| $R^6$ | H | H | H | H | $CH_3$ | $CH_3$ | $CH_3$ | $CH_3$ |
| $R^7$ | H | H | H | H | $CH_3$ | $CH_3$ | $CH_3$ | $CH_3$ |
| $R^8$ | H | H | H | H | $CH_3$ | $CH_3$ | $CH_3$ | $CH_3$ |
| $R^9$ | H | H | H | H | $CH_3$ | $CH_3$ | $CH_3$ | $CH_3$ |
| $R^{10}$ | H | H | H | H | $CH_3$ | $CH_3$ | $CH_3$ | $CH_3$ |

TABLE 2

| Compound | 9 | 10 | 11 | 12 | 13 | 14 | 15 | 16 |
|---|---|---|---|---|---|---|---|---|
| X | S | S | O | O | S | S | O | O |
| Y | O | — | O | — | O | — | O | — |
| $R^1$ | $C_2H_5$ | $C_2H_5$ | $C_2H_5$ | $C_2H_5$ | H | H | H | H |
| $R^2$ | $C_2H_5$ | $C_2H_5$ | $C_2H_5$ | $C_2H_5$ | H | H | H | H |
| $R^3$ | $C_2H_5$ | $C_2H_5$ | $C_2H_5$ | $C_2H_5$ | H | H | H | H |
| $R^4$ | $C_2H_5$ | $C_2H_5$ | $C_2H_5$ | $C_2H_5$ | H | H | H | H |
| $R^5$ | $C_2H_5$ | $C_2H_5$ | $C_2H_5$ | $C_2H_5$ | H | H | H | H |
| $R^6$ | $C_2H_5$ | $C_2H_5$ | $C_2H_5$ | $C_2H_5$ | $C_2H_5$ | $C_2H_5$ | $C_2H_5$ | $C_2H_5$ |
| $R^7$ | $C_2H_5$ | $C_2H_5$ | $C_2H_5$ | $C_2H_5$ | $C_2H_5$ | $C_2H_5$ | $C_2H_5$ | $C_2H_5$ |
| $R^8$ | $C_2H_5$ | $C_2H_5$ | $C_2H_5$ | $C_2H_5$ | $C_2H_5$ | $C_2H_5$ | $C_2H_5$ | $C_2H_5$ |
| $R^9$ | $C_2H_5$ | $C_2H_5$ | $C_2H_5$ | $C_2H_5$ | $C_2H_5$ | $C_2H_5$ | $C_2H_5$ | $C_2H_5$ |
| $R^{10}$ | $C_2H_5$ | $C_2H_5$ | $C_2H_5$ | $C_2H_5$ | $C_2H_5$ | $C_2H_5$ | $C_2H_5$ | $C_2H_5$ |

TABLE 3

| Compound | 17 | 18 | 19 | 20 | 21 | 22 | 23 | 24 |
|---|---|---|---|---|---|---|---|---|
| X | S | S | O | O | S | S | O | O |
| Y | O | — | O | — | O | — | O | — |
| $R^1$ | H | H | H | H | $CH_3$ | $CH_3$ | $CH_3$ | $CH_3$ |
| $R^2$ | H | H | H | H | H | H | H | H |
| $R^3$ | H | H | H | H | H | H | H | H |
| $R^4$ | H | H | H | H | H | H | H | H |
| $R^5$ | H | H | H | H | H | H | H | H |
| $R^6$ | $CH_3$ | $CH_3$ | $CH_3$ | $CH_3$ | $CH_3$ | $CH_3$ | $CH_3$ | $CH_3$ |
| $R^7$ | $CH_3$ | $CH_3$ | $CH_3$ | $CH_3$ | H | H | H | H |
| $R^8$ | $CH_3$ | $CH_3$ | $CH_3$ | $CH_3$ | H | H | H | H |
| $R^9$ | $CH_3$ | $CH_3$ | $CH_3$ | $CH_3$ | H | H | H | H |
| $R^{10}$ | $CH_3$ | $CH_3$ | $CH_3$ | $CH_3$ | H | H | H | H |

TABLE 4

| Compound | 25 | 26 | 27 | 28 | 29 | 30 | 31 | 32 |
|---|---|---|---|---|---|---|---|---|
| X | S | S | O | O | S | S | O | O |
| Y | O | — | O | — | O | — | O | — |
| $R^1$ | $CH_3$ | $CH_3$ | $CH_3$ | $CH_3$ | $CH_3$ | $CH_3$ | $CH_3$ | $CH_3$ |
| $R^2$ | $CH_3$ | $CH_3$ | $CH_3$ | $CH_3$ | H | H | H | H |
| $R^3$ | H | H | H | H | $CH_3$ | $CH_3$ | $CH_3$ | $CH_3$ |
| $R^4$ | H | H | H | H | H | H | H | H |
| $R^5$ | H | H | H | H | H | H | H | H |
| $R^6$ | $CH_3$ | $CH_3$ | $CH_3$ | $CH_3$ | $CH_3$ | $CH_3$ | $CH_3$ | $CH_3$ |
| $R^7$ | $CH_3$ | $CH_3$ | $CH_3$ | $CH_3$ | H | H | H | H |
| $R^8$ | H | H | H | H | $CH_3$ | $CH_3$ | $CH_3$ | $CH_3$ |
| $R^9$ | H | H | H | H | H | H | H | H |
| $R^{10}$ | H | H | H | H | H | H | H | H |

TABLE 5

| Compound | 33 | 34 | 35 | 36 | 37 | 38 | 39 | 40 |
|---|---|---|---|---|---|---|---|---|
| X | S | S | O | O | S | S | O | O |
| Y | O | — | O | — | O | — | O | — |
| $R^1$ | $CH_3$ | $CH_3$ | $CH_3$ | $CH_3$ | $CH_3$ | $CH_3$ | $CH_3$ | $CH_3$ |
| $R^2$ | $CH_3$ | $CH_3$ | $CH_3$ | $CH_3$ | $CH_3$ | $CH_3$ | $CH_3$ | $CH_3$ |
| $R^3$ | $CH_3$ | $CH_3$ | $CH_3$ | $CH_3$ | H | H | H | H |
| $R^4$ | H | H | H | H | $CH_3$ | $CH_3$ | $CH_3$ | $CH_3$ |
| $R^5$ | H | H | H | H | H | H | H | H |
| $R^6$ | $CH_3$ | $CH_3$ | $CH_3$ | $CH_3$ | $CH_3$ | $CH_3$ | $CH_3$ | $CH_3$ |
| $R^7$ | $CH_3$ | $CH_3$ | $CH_3$ | $CH_3$ | $CH_3$ | $CH_3$ | $CH_3$ | $CH_3$ |
| $R^8$ | $CH_3$ | $CH_3$ | $CH_3$ | $CH_3$ | H | H | H | H |
| $R^9$ | H | H | H | H | $CH_3$ | $CH_3$ | $CH_3$ | $CH_3$ |
| $R^{10}$ | H | H | H | H | H | H | H | H |

TABLE 6

| Compound | 41 | 42 | 43 | 44 | 45 | 46 | 47 | 48 |
|---|---|---|---|---|---|---|---|---|
| X | S | S | O | O | S | S | O | O |
| Y | O | — | O | — | O | — | O | — |
| $R^1$ | $CH_3$ | $CH_3$ | $CH_3$ | $CH_3$ | $C_2H_5$ | $C_2H_5$ | $C_2H_5$ | $C_2H_5$ |
| $R^2$ | $CH_3$ | $CH_3$ | $CH_3$ | $CH_3$ | H | H | H | H |
| $R^3$ | $CH_3$ | $CH_3$ | $CH_3$ | $CH_3$ | H | H | H | H |
| $R^4$ | $CH_3$ | $CH_3$ | $CH_3$ | $CH_3$ | H | H | H | H |
| $R^5$ | H | H | H | H | H | H | H | H |
| $R^6$ | $CH_3$ | $CH_3$ | $CH_3$ | $CH_3$ | $C_2H_5$ | $C_2H_5$ | $C_2H_5$ | $C_2H_5$ |
| $R^7$ | $CH_3$ | $CH_3$ | $CH_3$ | $CH_3$ | H | H | H | H |
| $R^8$ | $CH_3$ | $CH_3$ | $CH_3$ | $CH_3$ | H | H | H | H |
| $R^9$ | $CH_3$ | $CH_3$ | $CH_3$ | $CH_3$ | H | H | H | H |
| $R^{10}$ | H | H | H | H | H | H | H | H |

TABLE 7

| Compound | 49 | 50 | 51 | 52 | 53 | 54 | 55 | 56 |
|---|---|---|---|---|---|---|---|---|
| X | S | S | O | O | S | S | O | O |
| Y | O | — | O | — | O | — | O | — |
| $R^1$ | $C_2H_5$ | $C_2H_5$ | $C_2H_5$ | $C_2H_5$ | $C_2H_5$ | $C_2H_5$ | $C_2H_5$ | $C_2H_5$ |
| $R^2$ | $C_2H_5$ | $C_2H_5$ | $C_2H_5$ | $C_2H_5$ | H | H | H | H |
| $R^3$ | H | H | H | H | $C_2H_5$ | $C_2H_5$ | $C_2H_5$ | $C_2H_5$ |
| $R^4$ | H | H | H | H | H | H | H | H |
| $R^5$ | H | H | H | H | H | H | H | H |
| $R^6$ | $C_2H_5$ | $C_2H_5$ | $C_2H_5$ | $C_2H_5$ | $C_2H_5$ | $C_2H_5$ | $C_2H_5$ | $C_2H_5$ |

TABLE 7-continued

| Compound | 49 | 50 | 51 | 52 | 53 | 54 | 55 | 56 |
|---|---|---|---|---|---|---|---|---|
| $R^7$ | $C_2H_5$ | $C_2H_5$ | $C_2H_5$ | $C_2H_5$ | H | H | H | H |
| $R^8$ | H | H | H | H | $C_2H_5$ | $C_2H_5$ | $C_2H_5$ | $C_2H_5$ |
| $R^9$ | H | H | H | H | H | H | H | H |
| $R^{10}$ | H | H | H | H | H | H | H | H |

TABLE 8

| Compound | 57 | 58 | 59 | 60 | 61 | 62 | 63 | 64 |
|---|---|---|---|---|---|---|---|---|
| X | S | S | O | O | S | S | O | O |
| Y | O | — | O | — | O | — | O | — |
| $R^1$ | $C_2H_5$ | $C_2H_5$ | $C_2H_5$ | $C_2H_5$ | $C_2H_5$ | $C_2H_5$ | $C_2H_5$ | $C_2H_5$ |
| $R^2$ | $C_2H_5$ | $C_2H_5$ | $C_2H_5$ | $C_2H_5$ | $C_2H_5$ | $C_2H_5$ | $C_2H_5$ | $C_2H_5$ |
| $R^3$ | $C_2H_5$ | $C_2H_5$ | $C_2H_5$ | $C_2H_5$ | H | H | H | H |
| $R^4$ | H | H | H | H | $C_2H_5$ | $C_2H_5$ | $C_2H_5$ | $C_2H_5$ |
| $R^5$ | H | H | H | H | H | H | H | H |
| $R^6$ | $C_2H_5$ | $C_2H_5$ | $C_2H_5$ | $C_2H_5$ | $C_2H_5$ | $C_2H_5$ | $C_2H_5$ | $C_2H_5$ |
| $R^7$ | $C_2H_5$ | $C_2H_5$ | $C_2H_5$ | $C_2H_5$ | $C_2H_5$ | $C_2H_5$ | $C_2H_5$ | $C_2H_5$ |
| $R^8$ | $C_2H_5$ | $C_2H_5$ | $C_2H_5$ | $C_2H_5$ | H | H | H | H |
| $R^9$ | H | H | H | H | $C_2H_5$ | $C_2H_5$ | $C_2H_5$ | $C_2H_5$ |
| $R^{10}$ | H | H | H | H | H | H | H | H |

TABLE 9

| Compound | 65 | 66 | 67 | 68 | 69 | 70 | 71 | 72 |
|---|---|---|---|---|---|---|---|---|
| X | S | S | O | O | S | S | O | O |
| Y | O | — | O | — | O | — | O | — |
| $R^1$ | $C_2H_5$ | $C_2H_5$ | $C_2H_5$ | $C_2H_5$ | $C_2H_5$ | $C_2H_5$ | $C_2H_5$ | $C_2H_5$ |
| $R^2$ | $C_2H_5$ | $C_2H_5$ | $C_2H_5$ | $C_2H_5$ | $CH_3$ | $CH_3$ | $CH_3$ | $CH_3$ |
| $R^3$ | $C_2H_5$ | $C_2H_5$ | $C_2H_5$ | $C_2H_5$ | $CH_3$ | $CH_3$ | $CH_3$ | $CH_3$ |
| $R^4$ | $C_2H_5$ | $C_2H_5$ | $C_2H_5$ | $C_2H_5$ | $CH_3$ | $CH_3$ | $CH_3$ | $CH_3$ |
| $R^5$ | H | H | H | H | $CH_3$ | $CH_3$ | $CH_3$ | $CH_3$ |
| $R^6$ | $C_2H_5$ | $C_2H_5$ | $C_2H_5$ | $C_2H_5$ | $C_2H_5$ | $C_2H_5$ | $C_2H_5$ | $C_2H_5$ |
| $R^7$ | $C_2H_5$ | $C_2H_5$ | $C_2H_5$ | $C_2H_5$ | $CH_3$ | $CH_3$ | $CH_3$ | $CH_3$ |
| $R^8$ | $C_2H_5$ | $C_2H_5$ | $C_2H_5$ | $C_2H_5$ | $CH_3$ | $CH_3$ | $CH_3$ | $CH_3$ |
| $R^9$ | $C_2H_5$ | $C_2H_5$ | $C_2H_5$ | $C_2H_5$ | $CH_3$ | $CH_3$ | $CH_3$ | $CH_3$ |
| $R^{10}$ | H | H | H | H | $CH_3$ | $CH_3$ | $CH_3$ | $CH_3$ |

TABLE 10

| Compound | 73 | 74 | 75 | 76 | 77 | 78 | 79 | 80 |
|---|---|---|---|---|---|---|---|---|
| X | S | S | O | O | S | S | O | O |
| Y | O | — | O | — | O | — | O | — |
| $R^1$ | $C_2H_5$ | $C_2H_5$ | $C_2H_5$ | $C_2H_5$ | $C_2H_5$ | $C_2H_5$ | $C_2H_5$ | $C_2H_5$ |
| $R^2$ | $C_2H_5$ | $C_2H_5$ | $C_2H_5$ | $C_2H_5$ | $CH_3$ | $CH_3$ | $CH_3$ | $CH_3$ |
| $R^3$ | $CH_3$ | $CH_3$ | $CH_3$ | $CH_3$ | $C_2H_5$ | $C_2H_5$ | $C_2H_5$ | $C_2H_5$ |
| $R^4$ | $CH_3$ | $CH_3$ | $CH_3$ | $CH_3$ | $CH_3$ | $CH_3$ | $CH_3$ | $CH_3$ |
| $R^5$ | $CH_3$ | $CH_3$ | $CH_3$ | $CH_3$ | $CH_3$ | $CH_3$ | $CH_3$ | $CH_3$ |
| $R^6$ | $C_2H_5$ | $C_2H_5$ | $C_2H_5$ | $C_2H_5$ | $C_2H_5$ | $C_2H_5$ | $C_2H_5$ | $C_2H_5$ |
| $R^7$ | $C_2H_5$ | $C_2H_5$ | $C_2H_5$ | $C_2H_5$ | $C_2H_5$ | $C_2H_5$ | $C_2H_5$ | $C_2H_5$ |
| $R^8$ | $CH_3$ | $CH_3$ | $CH_3$ | $CH_3$ | $C_2H_5$ | $C_2H_5$ | $C_2H_5$ | $C_2H_5$ |
| $R^9$ | $CH_3$ | $CH_3$ | $CH_3$ | $CH_3$ | $CH_3$ | $CH_3$ | $CH_3$ | $CH_3$ |
| $R^{10}$ | $CH_3$ | $CH_3$ | $CH_3$ | $CH_3$ | $CH_3$ | $CH_3$ | $CH_3$ | $CH_3$ |

TABLE 11

| Compound | 81 | 82 | 83 | 84 | 85 | 86 | 87 | 88 |
|---|---|---|---|---|---|---|---|---|
| X | S | S | O | O | S | S | O | O |
| Y | O | — | O | — | O | — | O | — |
| $R^1$ | $C_2H_5$ | $C_2H_5$ | $C_2H_5$ | $C_2H_5$ | $C_2H_5$ | $C_2H_5$ | $C_2H_5$ | $C_2H_5$ |
| $R^2$ | $C_2H_5$ | $C_2H_5$ | $C_2H_5$ | $C_2H_5$ | $C_2H_5$ | $C_2H_5$ | $C_2H_5$ | $C_2H_5$ |
| $R^3$ | $C_2H_5$ | $C_2H_5$ | $C_2H_5$ | $C_2H_5$ | $CH_3$ | $CH_3$ | $CH_3$ | $CH_3$ |
| $R^4$ | $CH_3$ | $CH_3$ | $CH_3$ | $CH_3$ | $C_2H_5$ | $C_2H_5$ | $C_2H_5$ | $C_2H_5$ |
| $R^5$ | $CH_3$ | $CH_3$ | $CH_3$ | $CH_3$ | $CH_3$ | $CH_3$ | $CH_3$ | $CH_3$ |
| $R^6$ | $C_2H_5$ | $C_2H_5$ | $C_2H_5$ | $C_2H_5$ | $C_2H_5$ | $C_2H_5$ | $C_2H_5$ | $C_2H_5$ |
| $R^7$ | $C_2H_5$ | $C_2H_5$ | $C_2H_5$ | $C_2H_5$ | $C_2H_5$ | $C_2H_5$ | $C_2H_5$ | $C_2H_5$ |
| $R^8$ | $C_2H_5$ | $C_2H_5$ | $C_2H_5$ | $C_2H_5$ | $CH_3$ | $CH_3$ | $CH_3$ | $CH_3$ |
| $R^9$ | $CH_3$ | $CH_3$ | $CH_3$ | $CH_3$ | $C_2H_5$ | $C_2H_5$ | $C_2H_5$ | $C_2H_5$ |
| $R^{10}$ | $CH_3$ | $CH_3$ | $CH_3$ | $CH_3$ | $CH_3$ | $CH_3$ | $CH_3$ | $CH_3$ |

TABLE 12

| Compound | 89 | 90 | 91 | 92 | 93 | 94 | 95 | 96 |
|---|---|---|---|---|---|---|---|---|
| X | S | S | O | O | S | S | O | O |
| Y | O | — | O | — | O | — | O | — |
| $R^1$ | $C_2H_5$ | $C_2H_5$ | $C_2H_5$ | $C_2H_5$ | $C_2H_5$ | $C_2H_5$ | $C_2H_5$ | $C_2H_5$ |
| $R^2$ | $C_2H_5$ | $C_2H_5$ | $C_2H_5$ | $C_2H_5$ | $CH_3$ | $CH_3$ | $CH_3$ | $CH_3$ |
| $R^3$ | $C_2H_5$ | $C_2H_5$ | $C_2H_5$ | $C_2H_5$ | H | H | H | H |
| $R^4$ | $C_2H_5$ | $C_2H_5$ | $C_2H_5$ | $C_2H_5$ | H | H | H | H |
| $R^5$ | $CH_3$ | $CH_3$ | $CH_3$ | $CH_3$ | H | H | H | H |
| $R^6$ | $C_2H_5$ | $C_2H_5$ | $C_2H_5$ | $C_2H_5$ | $C_2H_5$ | $C_2H_5$ | $C_2H_5$ | $C_2H_5$ |
| $R^7$ | $C_2H_5$ | $C_2H_5$ | $C_2H_5$ | $C_2H_5$ | $CH_3$ | $CH_3$ | $CH_3$ | $CH_3$ |
| $R^8$ | $C_2H_5$ | $C_2H_5$ | $C_2H_5$ | $C_2H_5$ | H | H | H | H |
| $R^9$ | $C_2H_5$ | $C_2H_5$ | $C_2H_5$ | $C_2H_5$ | H | H | H | H |
| $R^{10}$ | $CH_3$ | $CH_3$ | $CH_3$ | $CH_3$ | H | H | H | H |

TABLE 13

| Compound | 97 | 98 | 99 | 100 | 101 | 102 | 103 | 104 |
|---|---|---|---|---|---|---|---|---|
| X | S | S | O | O | S | S | O | O |
| Y | O | — | O | — | O | — | O | — |
| $R^1$ | $C_2H_5$ | $C_2H_5$ | $C_2H_5$ | $C_2H_5$ | $C_2H_5$ | $C_2H_5$ | $C_2H_5$ | $C_2H_5$ |
| $R^2$ | H | H | H | H | $CH_3$ | $CH_3$ | $CH_3$ | $CH_3$ |
| $R^3$ | $CH_3$ | $CH_3$ | $CH_3$ | $CH_3$ | $CH_3$ | $CH_3$ | $CH_3$ | $CH_3$ |
| $R^4$ | H | H | H | H | H | H | H | H |
| $R^5$ | H | H | H | H | H | H | H | H |
| $R^6$ | $C_2H_5$ | $C_2H_5$ | $C_2H_5$ | $C_2H_5$ | $C_2H_5$ | $C_2H_5$ | $C_2H_5$ | $C_2H_5$ |
| $R^7$ | H | H | H | H | $CH_3$ | $CH_3$ | $CH_3$ | $CH_3$ |
| $R^8$ | $CH_3$ | $CH_3$ | $CH_3$ | $CH_3$ | $CH_3$ | $CH_3$ | $CH_3$ | $CH_3$ |
| $R^9$ | H | H | H | H | H | H | H | H |
| $R^{10}$ | H | H | H | H | H | H | H | H |

TABLE 14

| Compound | 105 | 106 | 107 | 108 | 109 | 110 | 111 | 112 |
|---|---|---|---|---|---|---|---|---|
| X | S | S | O | O | S | S | O | O |
| Y | O | — | O | — | O | — | O | — |
| $R^1$ | $C_2H_5$ | $C_2H_5$ | $C_2H_5$ | $C_2H_5$ | $C_2H_5$ | $C_2H_5$ | $C_2H_5$ | $C_2H_5$ |
| $R^2$ | $CH_3$ | $CH_3$ | $CH_3$ | $CH_3$ | $CH_3$ | $CH_3$ | $CH_3$ | $CH_3$ |
| $R^3$ | $CH_3$ | $CH_3$ | $CH_3$ | $CH_3$ | $CH_3$ | $CH_3$ | $CH_3$ | $CH_3$ |
| $R^4$ | $CH_3$ | $CH_3$ | $CH_3$ | $CH_3$ | H | H | H | H |
| $R^5$ | H | H | H | H | $CH_3$ | $CH_3$ | $CH_3$ | $CH_3$ |
| $R^6$ | $C_2H_5$ | $C_2H_5$ | $C_2H_5$ | $C_2H_5$ | $C_2H_5$ | $C_2H_5$ | $C_2H_5$ | $C_2H_5$ |
| $R^7$ | $CH_3$ | $CH_3$ | $CH_3$ | $CH_3$ | $CH_3$ | $CH_3$ | $CH_3$ | $CH_3$ |
| $R^8$ | $CH_3$ | $CH_3$ | $CH_3$ | $CH_3$ | $CH_3$ | $CH_3$ | $CH_3$ | $CH_3$ |
| $R^9$ | $CH_3$ | $CH_3$ | $CH_3$ | $CH_3$ | H | H | H | H |
| $R^{10}$ | H | H | H | H | $CH_3$ | $CH_3$ | $CH_3$ | $CH_3$ |

TABLE 15

| Compound | 113 | 114 | 115 | 116 | 117 | 118 | 119 | 120 |
|---|---|---|---|---|---|---|---|---|
| X | S | S | O | O | S | S | O | O |
| Y | O | — | O | — | O | — | O | — |
| $R^1$ | $C_2H_5$ | $C_2H_5$ | $C_2H_5$ | $C_2H_5$ | $C_2H_5$ | $C_2H_5$ | $C_2H_5$ | $C_2H_5$ |
| $R^2$ | $C_2H_5$ | $C_2H_5$ | $C_2H_5$ | $C_2H_5$ | $CH_3$ | $CH_3$ | $CH_3$ | $CH_3$ |
| $R^3$ | $CH_3$ | $CH_3$ | $CH_3$ | $CH_3$ | $C_2H_5$ | $C_2H_5$ | $C_2H_5$ | $C_2H_5$ |
| $R^4$ | H | H | H | H | H | H | H | H |
| $R^5$ | H | H | H | H | H | H | H | H |
| $R^6$ | $C_2H_5$ | $C_2H_5$ | $C_2H_5$ | $C_2H_5$ | $C_2H_5$ | $C_2H_5$ | $C_2H_5$ | $C_2H_5$ |
| $R^7$ | $C_2H_5$ | $C_2H_5$ | $C_2H_5$ | $C_2H_5$ | $CH_3$ | $CH_3$ | $CH_3$ | $CH_3$ |
| $R^8$ | $CH_3$ | $CH_3$ | $CH_3$ | $CH_3$ | $C_2H_5$ | $C_2H_5$ | $C_2H_5$ | $C_2H_5$ |

TABLE 15-continued

| Compound | 113 | 114 | 115 | 116 | 117 | 118 | 119 | 120 |
|---|---|---|---|---|---|---|---|---|
| $R^9$ | H | H | H | H | H | H | H | H |
| $R^{10}$ | H | H | H | H | H | H | H | H |

TABLE 16

| Compound | 121 | 122 | 123 | 124 | 125 | 126 | 127 | 128 |
|---|---|---|---|---|---|---|---|---|
| X | S | S | O | O | S | S | O | O |
| Y | O | — | O | — | O | — | O | — |
| $R^1$ | $C_2H_5$ | $C_2H_5$ | $C_2H_5$ | $C_2H_5$ | $C_2H_5$ | $C_2H_5$ | $C_2H_5$ | $C_2H_5$ |
| $R^2$ | H | H | H | H | $C_2H_5$ | $C_2H_5$ | $C_2H_5$ | $C_2H_5$ |
| $R^3$ | $C_2H_5$ | $C_2H_5$ | $C_2H_5$ | $C_2H_5$ | $CH_3$ | $CH_3$ | $CH_3$ | $CH_3$ |
| $R^4$ | H | H | H | H | $CH_3$ | $CH_3$ | $CH_3$ | $CH_3$ |
| $R^5$ | $CH_3$ | $CH_3$ | $CH_3$ | $CH_3$ | H | H | H | H |
| $R^6$ | $C_2H_5$ | $C_2H_5$ | $C_2H_5$ | $C_2H_5$ | $C_2H_5$ | $C_2H_5$ | $C_2H_5$ | $C_2H_5$ |
| $R^7$ | H | H | H | H | $C_2H_5$ | $C_2H_5$ | $C_2H_5$ | $C_2H_5$ |
| $R^8$ | $C_2H_5$ | $C_2H_5$ | $C_2H_5$ | $C_2H_5$ | $CH_3$ | $CH_3$ | $CH_3$ | $CH_3$ |
| $R^9$ | H | H | H | H | $CH_3$ | $CH_3$ | $CH_3$ | $CH_3$ |
| $R^{10}$ | $CH_3$ | $CH_3$ | $CH_3$ | $CH_3$ | H | H | H | H |

TABLE 17

| Compound | 129 | 130 | 131 | 132 | 133 | 134 | 135 | 136 |
|---|---|---|---|---|---|---|---|---|
| X | S | S | O | O | S | S | O | O |
| Y | O | — | O | — | O | — | O | — |
| $R^1$ | $C_2H_5$ | $C_2H_5$ | $C_2H_5$ | $C_2H_5$ | $C_2H_5$ | $C_2H_5$ | $C_2H_5$ | $C_2H_5$ |
| $R^2$ | $CH_3$ | $CH_3$ | $CH_3$ | $CH_3$ | H | H | H | H |
| $R^3$ | $C_2H_5$ | $C_2H_5$ | $C_2H_5$ | $C_2H_5$ | $C_2H_5$ | $C_2H_5$ | $C_2H_5$ | $C_2H_5$ |
| $R^4$ | $CH_3$ | $CH_3$ | $CH_3$ | $CH_3$ | $CH_3$ | $CH_3$ | $CH_3$ | $CH_3$ |
| $R^5$ | H | H | H | H | $CH_3$ | $CH_3$ | $CH_3$ | $CH_3$ |
| $R^6$ | $C_2H_5$ | $C_2H_5$ | $C_2H_5$ | $C_2H_5$ | $C_2H_5$ | $C_2H_5$ | $C_2H_5$ | $C_2H_5$ |
| $R^7$ | $CH_3$ | $CH_3$ | $CH_3$ | $CH_3$ | H | H | H | H |
| $R^8$ | $C_2H_5$ | $C_2H_5$ | $C_2H_5$ | $C_2H_5$ | $C_2H_5$ | $C_2H_5$ | $C_2H_5$ | $C_2H_5$ |
| $R^9$ | $CH_3$ | $CH_3$ | $CH_3$ | $CH_3$ | $CH_3$ | $CH_3$ | $CH_3$ | $CH_3$ |
| $R^{10}$ | H | H | H | H | $CH_3$ | $CH_3$ | $CH_3$ | $CH_3$ |

TABLE 18

| Compound | 137 | 138 | 139 | 140 | 141 | 142 | 143 | 144 |
|---|---|---|---|---|---|---|---|---|
| X | S | S | O | O | S | S | O | O |
| Y | O | — | O | — | O | — | O | — |
| $R^1$ | $C_2H_5$ | $C_2H_5$ | $C_2H_5$ | $C_2H_5$ | $C_2H_5$ | $C_2H_5$ | $C_2H_5$ | $C_2H_5$ |
| $R^2$ | $C_2H_5$ | $C_2H_5$ | $C_2H_5$ | $C_2H_5$ | $C_2H_5$ | $C_2H_5$ | $C_2H_5$ | $C_2H_5$ |
| $R^3$ | $C_2H_5$ | $C_2H_5$ | $C_2H_5$ | $C_2H_5$ | $CH_3$ | $CH_3$ | $CH_3$ | $CH_3$ |
| $R^4$ | $CH_3$ | $CH_3$ | $CH_3$ | $CH_3$ | $C_2H_5$ | $C_2H_5$ | $C_2H_5$ | $C_2H_5$ |
| $R^5$ | H | H | H | H | H | H | H | H |
| $R^6$ | $C_2H_5$ | $C_2H_5$ | $C_2H_5$ | $C_2H_5$ | $C_2H_5$ | $C_2H_5$ | $C_2H_5$ | $C_2H_5$ |
| $R^7$ | $C_2H_5$ | $C_2H_5$ | $C_2H_5$ | $C_2H_5$ | $C_2H_5$ | $C_2H_5$ | $C_2H_5$ | $C_2H_5$ |
| $R^8$ | $C_2H_5$ | $C_2H_5$ | $C_2H_5$ | $C_2H_5$ | $CH_3$ | $CH_3$ | $CH_3$ | $CH_3$ |
| $R^9$ | $CH_3$ | $CH_3$ | $CH_3$ | $CH_3$ | $C_2H_5$ | $C_2H_5$ | $C_2H_5$ | $C_2H_5$ |
| $R^{10}$ | H | H | H | H | H | H | H | H |

Lubricating oils and greases, for example, can be cited as lubricating compositions of this invention. The amount of a compound of this invention in a lubricating composition is the same as with the conventional friction-modifiers, for example, being compounded in a proportion with respect to the composition generally of some 0.1 to 10 wt %.

There are no particular limitations regarding the base oil or grease used in lubricating composition according to the present invention, and various conventional greases, mineral oils and synthetic oils may be conveniently used. For the purpose of this description, the term "base oil" is meant to also include a grease base stock.

The base oil used in the present invention may conveniently comprise mixtures of one or more mineral oils and/or one or more synthetic oils.

Mineral oils include liquid petroleum oils and solvent-treated or acid-treated mineral lubricating oil of the paraffinic, naphthenic, or mixed paraffinic/naphthenic type which may be further refined by hydrofinishing processes and/or dewaxing.

Suitable base oils for use in the lubricating oil composition of the present invention are Group I, Group II or Group III base oils, polyalphaolefins, Fischer-Tropsch derived base oils and mixtures thereof.

By "Group I" base oil, "Group II" base oil and "Group III" base oil in the present invention are meant lubricating oil base oils according to the definitions of American Petroleum Institute (API) categories I, II and III. Such API categories are defined in API Publication 1509, 15th Edition, Appendix E, April 2002.

Suitable Fischer-Tropsch derived base oils that may be conveniently used as the base oil in the lubricating oil composition of the present invention are those as for example disclosed in EP 0 776 959, EP 0 668 342, WO 97/21788, WO 00/15736, WO 00/14188, WO 00/14187, WO 00/14183, WO 00/14179, WO 00/08115, WO 99/41332, EP 1 029 029, WO 01/18156 and WO 01/57166.

Synthetic oils include hydrocarbon oils such as olefin oligomers (PAOs), dibasic acid esters, polyol esters, and dewaxed waxy raffinate. Synthetic hydrocarbon base oils sold by the Shell Group under the designation "XHVI" (trade mark) may be conveniently used.

Effects of the Invention (1) Novel phosphorus-free Mo-based friction-modifiers have been obtained.
(2) The compounds of this invention exhibit a low friction coefficient and they can be used in particular as friction modifiers for various types of energy-saving engine lubricating oils.
(3) The compounds of this invention are especially suitable for use as friction-modifiers for fuel-saving engine oils as they are phosphorus-free.
(4) There is no damage to the catalysts (removal of NOx) which are housed in automobile exhaust gas cleaning apparatus.

EXAMPLES

The invention is described below by means of Examples and Comparative Examples but the invention is not limited in any way by these examples.

Example 1

The synthesis of Compound 6 in the aforementioned Table 1, the case where X is S, there is no Y and $R^1$ to $R^{10}$ are $CH_3$.

(i) First Process

Tetrahydrofuran (THF, 45 ml) was added to 3.75 g (18.8 mmol) of pentamethylcyclopentadiene and, after being cooled to −78° C., 12.5 ml (18.8 mmol) of Bu—Li were added dropwise and lithium pentamethylcyclopentadienyl was co-ordinated. Then 5 g (18.8 mmol) of molybdenum hexa-carbonyl were added to this material and heated under reflux for 48 hours and, after the reaction had been completed, the mother liquor was cooled to 0° C. Separately, 3.2 g (18.8 mmol) of iron(II) sulphate was added to a solution comprising a mixture of 100 ml of pure water and 20 ml of acetic acid and the solution so obtained was added dropwise to the mother liquor. The red coloured solution obtained was subjected to suction filtration, washed and dried and the di(pentamethylcyclopentadienyl)molybdenum hexa-carbonyl complex was obtained by recrystallization. Yield 24%

(ii) Second Process

The di(pentamethylcyclopentadienyl)molybdenum hexa-carbonyl complex (0.5 g, 0.79 mmol) and 0.69 g (5.84 mmol) of 3-sulphorane were dissolved in 100 ml of toluene and heated under reflux at 120° C. for 3 hours. After the reaction had been completed the solvent was removed and the reaction product was subjected to column chromatography and a red coloured complex was isolated. Yield 3%

Example 2

The synthesis of Compound 5 in the aforementioned Table 1, the case where X is S, Y is O and $R^1$ to $R^{10}$ are $CH_3$.

The aforementioned di(heptamethylcyclopentadienyl) molybdenum hexa-carbonyl complex (0.5 g, 0.79 mmol) and 0.69 g (5.84 mmol) of 3-sulphorane were dissolved in 100 ml of toluene and heated under reflux at 120° C. for 3 hours. After the reaction had been completed the solvent was removed and the reaction product was subjected to column chromatography and an orange coloured complex was isolated. Yield 4%

Example 3

The synthesis of Compound 3 in the aforementioned Table 1, the case where X and Y are O and $R^1$ to $R^{10}$ are H.

(i) First Process

Tetrahydrofuran (THF, 45 ml) was added to 18.8 mmol of cyclopentadiene and, after being cooled to −78° C., 12.5 ml (18.8 mmol) of Bu—Li were added dropwise and the lithium pentamethylcyclopentadienyl was co-ordinated. Then 5 g (18.8 mmol) of molybdenum hexa-carbonyl were added to this material and heated under reflux for 48 hours and, after the reaction had been completed, the mother liquor was cooled to 0° C. Separately, 3.2 g (18.8 mmol) of iron(II) sulphate was added to a solution comprising a mixture of 100 ml of pure water and 20 ml of acetic acid and the solution so obtained was added dropwise to the mother liquor. The red coloured solution obtained was subjected to suction filtration, washed and dried and the di(cyclopentadienyl)molybdenum hexa-carbonyl complex was obtained by recrystallization. Yield 20%

(ii) Second Process

The di(cyclopentadienyl)molybdenum hexa-carbonyl complex (0.5 g, 1.02 mmol) and 0.6 g (5.08 mmol) of 3-sulphorane were dissolved in 50 ml of toluene and heated under reflux at 120° C. for 3 hours. After removing the solvent the yellow coloured product di(cyclopentadienyl) μ-oxodioxomolybdenum complex was produced and isolated from the reaction mixture by means of column chromatography. Yield 34%

Example 4

The synthesis of Compound 1 in the aforementioned Table 1, the case where X is S, Y is O and $R^1$ to $R^{10}$ are H.

Reaction in the same way as in Example 3 and the red coloured product di(cyclopentadienyl) μ-thioxodioxomolybdenum complex was isolated by means of column chromatography. Yield 14%

Example 5

The complex obtained in Example 2 was adjusted in such a way as to provide an Mo content of 500 ppm in engine oil (di-isononyl adipic acid) (viscosity at 100° C.: 3.04 mm²/s) to which 5% of a dispersing agent (alkenylsuccinic acid polyalkylene polyimide, trade name Infineum C9266) had been added.

Comparative Example 1

The case where the complex obtained in Example 2 had not been used in the composition of Example 5 was taken as Comparative Example 1. Both of the compositions are shown in Table 20 below.

Figure 1:
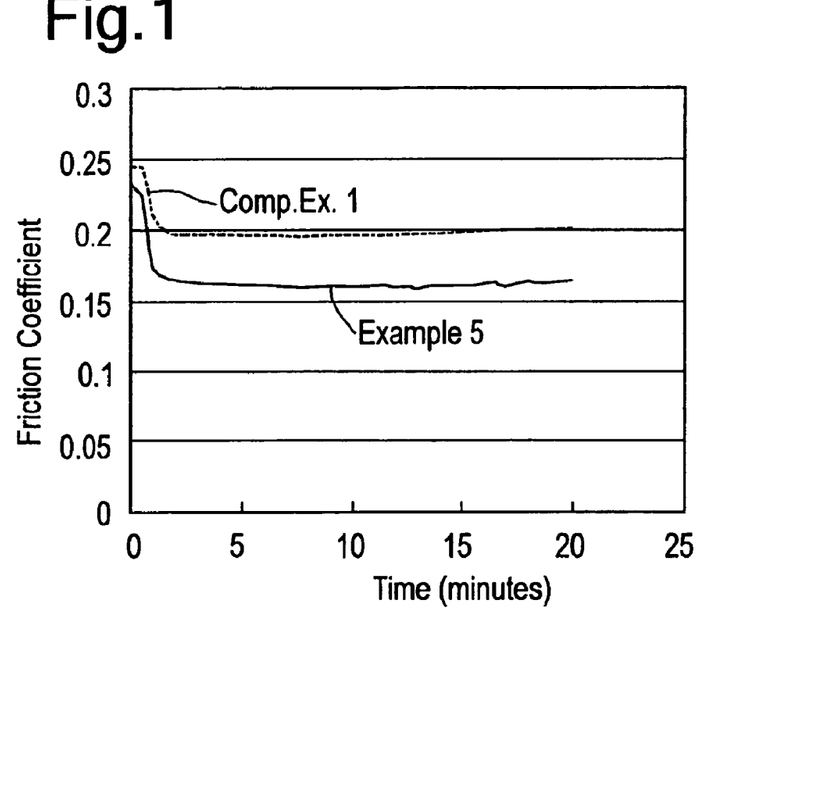
FIG. 1 is a graph showing how the friction coefficient changed with the passage of time with the lubricating oils of Example 5 and Comparative Example 1.
Figure 2:
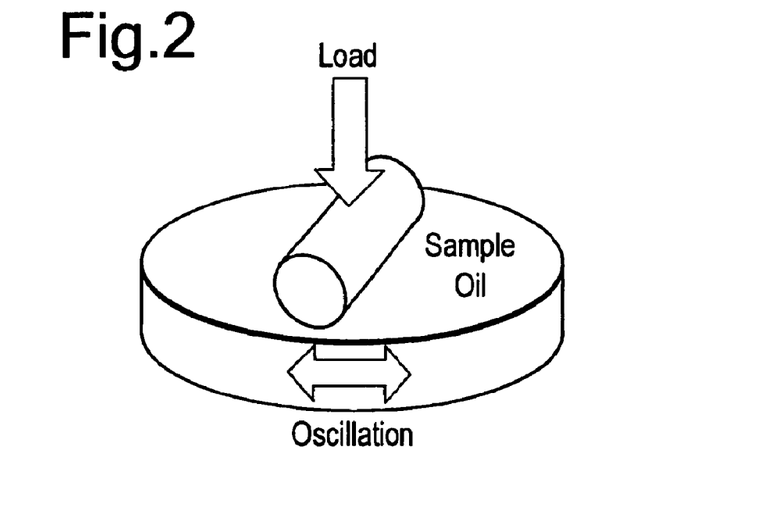
FIG. 2 is an outline drawing of the cylinder-on-disc reciprocating movement tester.

These sample oils were subjected to 30 minute friction coefficient measurement and evaluation under the conditions shown in Table 19 below using an SRV tester (a reciprocating movement tester of the cylinder-on-disc type shown in FIG. 2) and the results are shown in FIG. 1. The test piece was 52100 steel.

Testing Conditions

TABLE 19

| Condition | Parameter |
|---|---|
| Load | 400N |
| Frequency | 50 Hz |
| Amplitude | 1.5 mm |
| Temperature | 100° C. |
| Sample Size | 0.5 mm³ |

TABLE 20

| | Comparative Example 1 | Example 5 |
|---|---|---|
| Base Oil | Ester oil (di-isononyl adipic acid) | Ester oil (di-isononyl adipic acid) |
| Friction-modifier | Not added | Complex obtained in Example 2 |
| Mo Content in the Oil ppm | 0 | 500 |
| Alkenylsuccinic acid polyalkylene polyimide (%) | 5 | 5 |

The case of the Example 5 exhibited a low friction coefficient when compared with the base oil with no addition (Comparative Example 1) from 1 minute after the start of the test and it is clear that the compound had the function of a friction-modifier. That is to say, the compounding of a friction-modifier of this invention clearly shows a lower friction coefficient when compared with the case where it has not been compounded.

What is claimed is:

1. A lubricating composition comprising a base oil and a dicyclo-pentadienyl molybdenum crosslinked complex having general formula (1) below

General Formula (1)

wherein X is the element oxygen or the element sulphur, Y is the element oxygen or Y is absent, and $R^1$ to $R^{10}$ are groups selected individually from the group comprising hydrogen, a methyl group and an ethyl group.

2. The lubricating composition according to claim 1 wherein the dicyclopentadienyl molybdenum crosslinked complex has general formula (2) below

General Formula (2)

wherein $R^1$ to $R^{10}$ are groups selected individually from the group comprising hydrogen, a methyl group and an ethyl group.

3. The lubricating composition according to claim 1 wherein the dicyclopentadienyl molybdenum crosslinked complex has general formula (3) below General Formula (3)

(3)

wherein $R^1$ to $R^{10}$ are groups selected individually from the group comprising hydrogen, a methyl group and an ethyl group.

4. The lubricating composition according to claim 1 wherein the dicyclopentadienyl molybdenum crosslinked complex has general formula (4) below General Formula (4)

(4)

wherein $R^1$ to $R^{10}$ are groups selected individually from the group comprising hydrogen, a methyl group and an ethyl group.

5. The lubricating composition according to claim 1 wherein the dicyclopentadienyl molybdenum crosslinked complex has general formula (5) below General Formula (5)

(5)

wherein $R^1$ to $R^{10}$ are groups selected individually from the group comprising hydrogen, a methyl group and an ethyl group.

6. A method of improving the friction characteristics of a lubricating composition by using the dicyclopentadienyl molybdenum crosslinked complex as defined in claim 1.

7. A method of improving friction characteristics by lubricating with a lubricating composition according to claim 1.

* * * * *